(12) United States Patent
Furey

(10) Patent No.: US 8,501,460 B2
(45) Date of Patent: *Aug. 6, 2013

(54) BIOREACTOR SYSTEMS AND DISPOSABLE BIOREACTOR

(75) Inventor: James Francis Furey, Brookline, MA (US)

(73) Assignee: Mayfair Technology Limited Liability Company, Plainsboro, NJ (US)

( * ) Notice: Subject to any disclaimer, the term of this patent is extended or adjusted under 35 U.S.C. 154(b) by 195 days.

This patent is subject to a terminal disclaimer.

(21) Appl. No.: 13/008,553

(22) Filed: Jan. 18, 2011

(65) Prior Publication Data

US 2011/0111486 A1    May 12, 2011

Related U.S. Application Data

(63) Continuation of application No. 11/009,915, filed on Dec. 13, 2004, now Pat. No. 7,875,448.

(60) Provisional application No. 60/535,965, filed on Jan. 12, 2004.

(51) Int. Cl.
*C12M 1/02* (2006.01)

(52) U.S. Cl.
USPC .................. 435/287.2; 435/287.4; 435/289.1; 435/296.1

(58) Field of Classification Search
USPC ...... 435/289.1, 296.1, 297.2, 813; 261/122.1; 366/137
See application file for complete search history.

(56) References Cited

U.S. PATENT DOCUMENTS

| | | | |
|---|---|---|---|
| 2,277,120 A | 3/1942 | Lindsey | |
| 2,342,559 A | 2/1944 | Sebald | |
| 2,854,792 A | 10/1958 | Juda | |
| 2,865,618 A | 12/1958 | Abell | |
| 3,705,082 A | 12/1972 | Hondermarck et al. | |
| 3,814,003 A | 6/1974 | Vacano | |
| 3,910,826 A | 10/1975 | Kataoka | |
| 3,986,297 A | 10/1976 | Ichimura et al. | |
| 4,041,180 A | 8/1977 | Wilson | |
| 4,202,774 A | 5/1980 | Kos | |
| 4,660,988 A | 4/1987 | Hara et al. | |
| 4,738,540 A | 4/1988 | Banks | |
| 5,622,857 A | 4/1997 | Goffe | |
| 5,688,687 A | 11/1997 | Palsson | |
| 6,029,660 A | 2/2000 | Calluaud et al. | |
| 6,048,721 A | 4/2000 | Armstrong | |
| 6,168,949 B1 | 1/2001 | Rubenberger | |
| 6,391,638 B1 | 5/2002 | Shaaltiel | |
| 6,432,698 B1 | 8/2002 | Gaugler | |
| 6,544,424 B1 | 4/2003 | Shevitz | |
| 6,544,788 B2 | 4/2003 | Singh | |
| 6,551,805 B2 | 4/2003 | Ho et al. | |
| 7,875,448 B2 * | 1/2011 | Furey | 435/289.1 |

(Continued)

FOREIGN PATENT DOCUMENTS

| | | |
|---|---|---|
| GB | 2202549 | 9/1988 |
| JP | 63146780 | 6/1988 |

(Continued)

*Primary Examiner* — William H Beisner
(74) *Attorney, Agent, or Firm* — Hoffmann & Baron, LLP

(57) ABSTRACT

The present invention is in the field of cell bioreactors, and specifically in the field of disposable bioreactors.

21 Claims, 10 Drawing Sheets

| U.S. PATENT DOCUMENTS | | | | FOREIGN PATENT DOCUMENTS | | |
|---|---|---|---|---|---|---|
| 2002/0110915 A1 | 8/2002 | Shaaltiel | | JP | 01268561 A * | 10/1989 |
| 2003/0036192 A1 | 2/2003 | Singh | | JP | 02031826 | 2/1990 |
| 2003/0119185 A1 | 6/2003 | Berenson | | WO | WO 2004/039949 | 5/2004 |
| 2003/0235908 A1 | 12/2003 | Berenson | | | | |
| 2004/0110273 A1 | 6/2004 | Akers | | * cited by examiner | | |

BIOREACTOR SYSTEMS AND DISPOSABLE BIOREACTOR

CROSS-REFERENCE TO RELATED APPLICATIONS

This application claims priority to U.S. Provisional Application 60/535,965 filed on Jan. 12, 2004, as well as priority to U.S. Non-Provisional patent application Ser. No. 11/009,915 filed Dec. 13, 2004 now U.S. Pat. No. 7,875,448, which are both hereby incorporated by reference in their entirety.

FIELD OF THE INVENTION

The present invention is in the field of cell bioreactors, and specifically in the field of disposable bioreactors.

BACKGROUND

Since the advent of the biotechnology revolution, there has been a desire to grow cells in culture and a need to separate components in these fluid systems. Such separation has been accomplished by a multitude of methods, including, for example, through centrifugation, ion exchange columns, and physical filtering, among many others.

Bioreactors, which are typically chambers in which a cell culture is grown, have been produced in many forms. Frequently, bioreactors are used to grow a mammalian cell culture in which the cells produce an extracellular component, such as an antibody or recombinant protein. Bioreactors are also used for virus production. A separation process is performed in order to concentrate and purify the desired component from the bioreactor, which may, for example, be useful as a therapeutic or diagnostic agent.

One bioreactor configuration uses an impeller to constantly mix a liquid growth medium that has been inoculated with a cell culture. Ports in the bioreactor allow for nutrients to be added, contents to be removed, and sensing of various growth parameters, such as dissolved oxygen content and pH. In batch systems the growing culture is allowed to grow to a point at which the desired component is believed to be at optimal concentration, and then the entire vessel is harvested to separate the cells from the medium for secreted products. This separation is typically done by filtration or centrifugation. In contrast to batch systems, in a perfusion bioreactor, at some point after culture inoculation, the liquid media is circulated out of the bioreactor, through a separation device, and then returned to the bioreactor. The separation device is typically a filtration device, centrifuge, or a settling device. The separation device selectively removes a percentage of the contents, including any secreted product and cell waste product, of the liquid stream from the bioreactor. The volume removed is replaced to the bioreactor with growth medium. In these types of systems, separation can occur for an extended period of time, as long as wastes are removed and the culture medium is replenished, as needed.

With either of these batch or perfusion systems, however, the complexity of the systems and the frequent requirement to sterilize parts before use and thoroughly clean after use adds to the overall cost and reduces the efficiency of the cell culture production and filtration process. There is therefore a need in the art for bioreactors, bioreactor systems, and filtration devices that allow for the efficient production of biological components from a cell culture.

A recent technology for biological filtration involves the use of hollow fiber technology. Hollow fiber filters typically have a plurality of relatively thin, fiber tubes that are arranged in parallel to one another. A fluid having at least one biological component is passed through the wall of the tubes, which are designed to allow for the passage of very small components, along with the fluid from the vessel. The fluid and components that are small enough to pass through the hollow fiber wall of a specified size is then collected. The fluid that passes through, either with or without the desired biological component, is present in a more pure form relative to the starting fluid. This filtration process is made significantly more efficient by the flowing of the liquid medium that occurs along the walls of the hollow fibers. The flow of that liquid causes the constant removal of material from the inner walls of the fiber tubes that would otherwise quickly clog the fibers and prevent filtration.

Hollow fiber filtration can be used to filter many types of biological components. A very common system that employs hollow fiber filtration utilizes a bioreactor.

SUMMARY OF THE INVENTION

Now, according to the present invention, a bioreactor that efficiently uses a liquid diffuser to effect mixing of a cell culture is provided. Bioreactor valving systems that effectively utilize diaphragm pump technology are provided. Further, hollow fiber filters that are easily and economically used are provided.

The present invention includes a disposable bioreactor, comprising: a container; a liquid diffuser disposed within said container; and, a tube connecting said liquid diffuser to the outside of said container.

The present invention includes a bioreactor valve system, comprising: a first unidirectional valve; a second unidirectional valve; means for connecting said first unidirectional valve and said second unidirectional valve to a diaphragm pump; and, means for connecting said first unidirectional valve and said second unidirectional valve to a bioreactor, wherein said first unidirectional valve allows liquid flow away from said bioreactor and toward said diaphragm pump and said second unidirectional valve allows liquid flow toward said bioreactor and away from said diaphragm pump.

The present invention includes a disposable filter, comprising: a filter housing having an open first end and an open second end, wherein said open second end is formed in the shape of the liquid-containing side of a diaphragm pump; and, a filter element disposed in said filter housing.

The present invention includes a disposable filtration system, comprising at least two of the following three components: A) a disposable bioreactor, comprising: a container; a liquid diffuser disposed within said container; and, a tube connecting said liquid diffuser to the outside of said container; B) a bioreactor valve system, comprising:
a first unidirectional valve; a second unidirectional valve; means for connecting said first unidirectional valve and said second unidirectional valve to a diaphragm pump; and, means for connecting said first unidirectional valve and said second unidirectional valve to a bioreactor, wherein said first unidirectional valve allows liquid flow away from said bioreactor and toward said diaphragm pump and said second unidirectional valve allows liquid flow toward said bioreactor and away from said diaphragm pump; and, C) a disposable filter, comprising: a filter housing having an open first end and an open second end, wherein said open second end is formed in the shape of the liquid-containing side of a diaphragm pump; and, a filter element disposed in said filter housing.

DETAILED DESCRIPTION

The present invention provides bioreactors, bioreactor valving systems, integrated filters, bioreactor systems, and methods of manufacturing and using all of the foregoing.

Conventional bioreactors for growing cell cultures are manufactured in many different forms. Most, however, seek to achieve the same goal, which is the maximization of one or more cellular products, for example antibodies, proteins, or viruses.

Variations include a cassette type bioreactor (U.S. Pat. No. 5,688,687), bioreactors that use air mixing techniques (U.S. Patent Application 2002/0110915, U.S. Pat. No. 6,432,698), complicated, concentric hollow fiber bundle bioreactors (U.S. Pat. No. 5,622,857), and a bioreactor that uses a back and forth seesaw motion to achieve fluid movement (U.S. Pat. No. 6,544,788), among many others.

Figure 1:
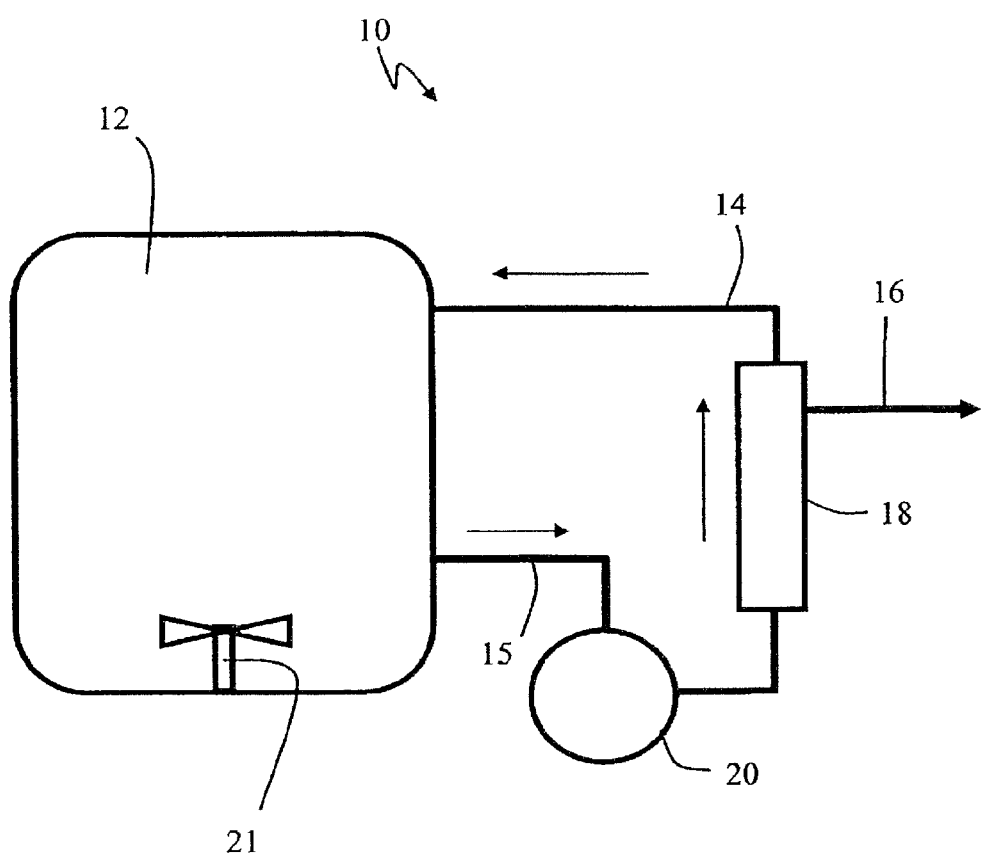
FIG. 1 is a schematic representation of a conventional bioreactor filtration system.

One example of a conventional bioreactor system is shown generally at 10 in FIG. 1. As shown schematically in FIG. 1, a bioreactor container 12 is provided to hold a fluid culture medium. An impeller 21 is incorporated within the container 12 to allow for mixing of the culture medium. A filter outlet tube 15 is provided to allow culture to be withdrawn from the container 12. A pump 20 is used to pull the media out of the container and force it through a filter 18 which in this case is a hollow fiber filter (fluid directional flow is shown with arrows). Hollow fiber filters can be disposable units having a plastic housing, or can be a unit having a permanent housing into which disposable filter cartridges are inserted.

The pressurized media is forced out of the filter 18 and into a return tube 14. Filtered media is collected through a filtrate collection port (not shown) on the filter 18 housing and passed through a filtrate collection tube 16. A pump (not shown), can optionally be included to control the flow of filtrate from the filter 18.

Figure 2:
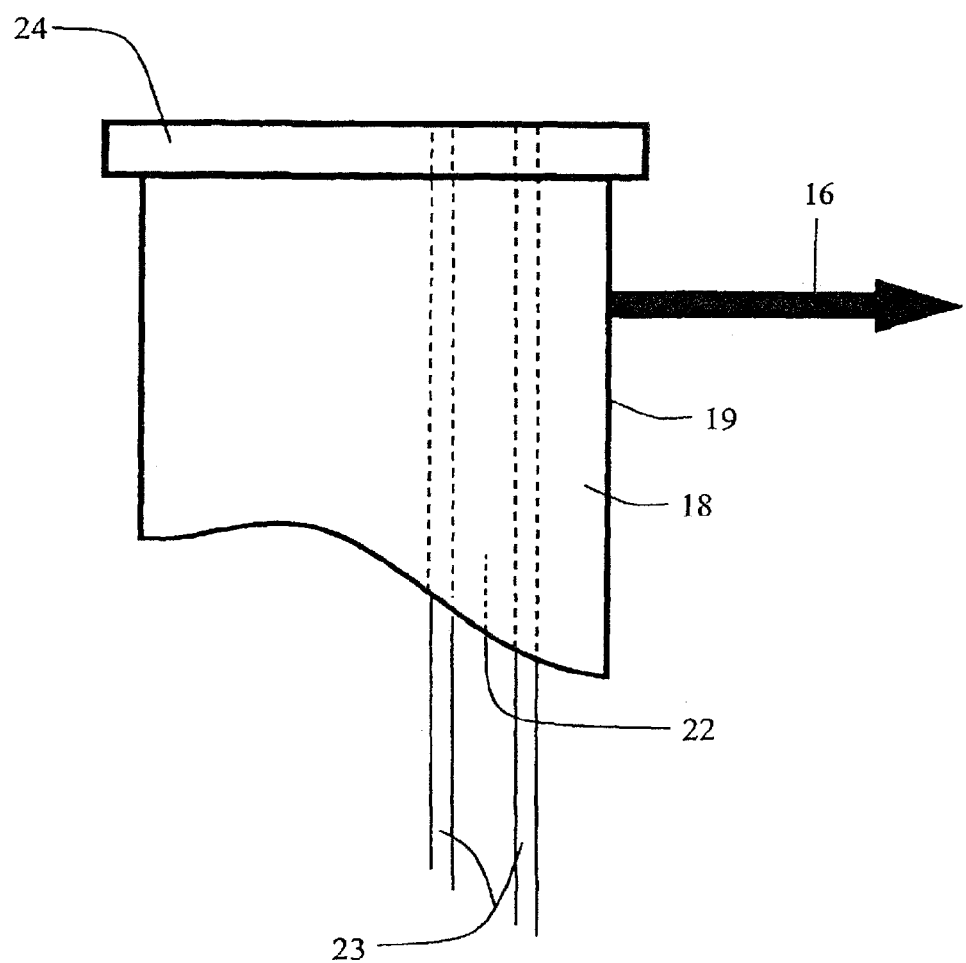
FIG. 2 is a schematic representation of a cutaway view of a hollow fiber filter.

The conventional system shown in FIG. 1 uses a hollow fiber filter, which is shown in more detail in FIG. 2. As shown in FIG. 2, which shows a cutaway view of one end of a hollow fiber filter 18, the filter housing 19 contains a plurality of cylindrical, hollow fibers 23 disposed in parallel in a bundle that extends from a first end 24 to a second end (not shown). For clarity, only two hollow fibers 23 are shown in FIG. 2.

The hollow fibers 23 are sealed at the first end 24 and the second end in such a manner so that a space 22 is defined within the filter housing 19 that is bound by the internal surface of the filter housing 19, the external surfaces of the hollow fibers 23, and the sealant material (not shown) that is used to seal the first end 24 and the second end around the ends of the hollow fibers.

As is well known in the art, if a liquid is forced under pressure through the lumens of the hollow fibers 23, most of the liquid will pass through the hollow fibers 23 and out of the second end of the filter. Some of the liquid, however, and any biological components present in the liquid that are smaller than the filtration size of the hollow fibers 23, will pass through the walls of the hollow fibers 23 and accumulate in the space 22 defined within the filter housing 19. The fluid and components that collect in the space 22 is known as the filtrate. The filtrate is removed from the filter 18 through a port (not shown) in the filter housing 19 and through a filtrate tube 16. Optionally, a pump (not shown) can be installed in the filtrate tube 16 line to control the flow of filtrate from the filter 18.

A significant benefit obtained by using a system such as the one shown in FIG. 1 is that the cell culture in the container can be grown at a high cell concentration and kept there for extended periods of time relative to a batch culture in a productive state by adding nutrients and removing waste, as required. The system shown can also be used for a batch culture for growth and harvest. Further, the hollow fiber filter 18 allows extended filtration because the liquid passing through the lumens of the hollow fibers 23 acts to wash trapped materials away from the inner walls of the hollow fibers, thereby preventing clogging of the fibers. This continuous growth type system, or perfusion system, allows for greater yields and greater efficiency than can be obtained with similar sized batch cultures.

Figure 3:
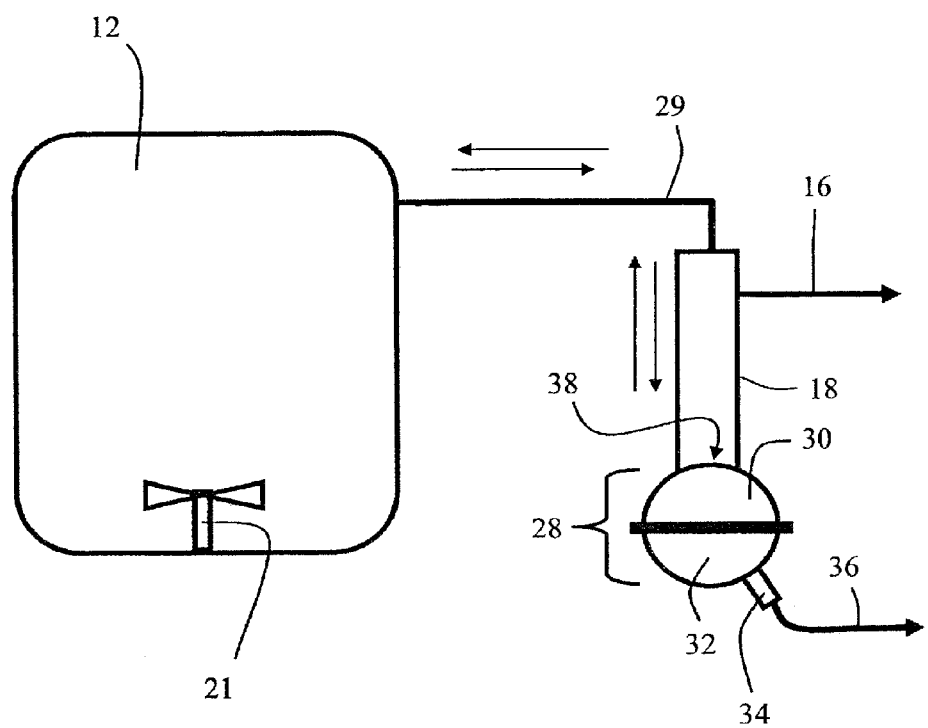
FIG. 3 is a schematic representation of a diaphragm pump bioreactor filtration system.

A variation on the perfusion system shown in FIG. 1 is provided in FIG. 3. As shown in FIG. 3, a reverse cross flow system (also known as alternating tangential flow, or ATF) does not rely on a filtration loop, where fluid flows in only one direction, but rather uses a back and forth flow to achieve a similar result. The back and forth flow in the system shown in FIG. 3 is obtained by using a diaphragm pump 28 that has a liquid-containing side 30 and a gas-containing side 32. In the example shown, the diaphragm pump is roughly spherical, and the liquid-containing side 30 and the gas-containing side 32 are each roughly hemispherical. The diaphragm pump 28 is attached to the filter 18 at a joint 38. A gas port 34 connects the internal space of the gas-containing side 32 to a gas supply line 36, which is connected to a device (not shown) that is capable of increasing or decreasing the pressure of the gas in the gas-containing side 32. The gas-containing side 32 and the liquid-containing side 30 are separated by a flexible liquid impermeable membrane, or diaphragm (not shown).

The system in FIG. 3 functions through the application and removal of pressure to the gas-containing side 32 of the diaphragm pump 28. Upon a reduction of pressure, the membrane is drawn into the gas-containing side, and an equivalent volume of fluid is drawn through a dual outlet and return connector tube 29, through the fibers of the filter 18, and into the liquid-containing side 30 of the diaphragm pump, essentially filling the complete volume of the diaphragm pump 28. Upon application of pressure thereafter, the membrane is forced into the liquid-containing side 30 of the diaphragm pump 28, and the fluid inside of the diaphragm pump 28 is forced back through the fibers of the filter 18 and the tube 29 to the container 12. In this manner, a similar filtration effect to that achieved in the system shown in FIG. 1 is achieved. The significant advantage of this reverse cross flow system over the prior system is that the diaphragm pump 28 causes less mechanical damage, shearing and otherwise, to the intact cells and cellular components in the cell culture.

One example of the system shown in FIG. 3 is provided in U.S. Pat. No. 6,544,424, which describes a reverse cross flow system using a conventional bioreactor. There are several drawbacks to the system shown in FIG. 3. One drawback is the use of a conventional impeller to mix the cell culture in the bioreactor container. The use of an impeller not only causes mechanical damage to the cells and cellular components in the cell culture, but also necessitates an additional aperture in the container wall and requires the use of motor. Further, because the outlet and return tube functions as both the outlet tube and the return tube, the outlet and return tube used to connect the bioreactor container to the filter limits return of culture to the vessel for medium and oxygen exchange. Further, in a conventional system such as the one described in U.S. Pat. No. 6,544,424, the entire diaphragm pump is manufactured as a permanent component that needs to be cleaned and sterilized after every use, which not only reduces efficiency, but also adds complexity to the system because a joint (shown as 38 in FIG. 3) is required to join the filter to the diaphragm pump.

The present invention solves the above listed problems in several ways, thereby allowing a more efficient and cost effective system to be used for growing cell cultures and the filtration of biological components from a liquid medium.

Figure 4:
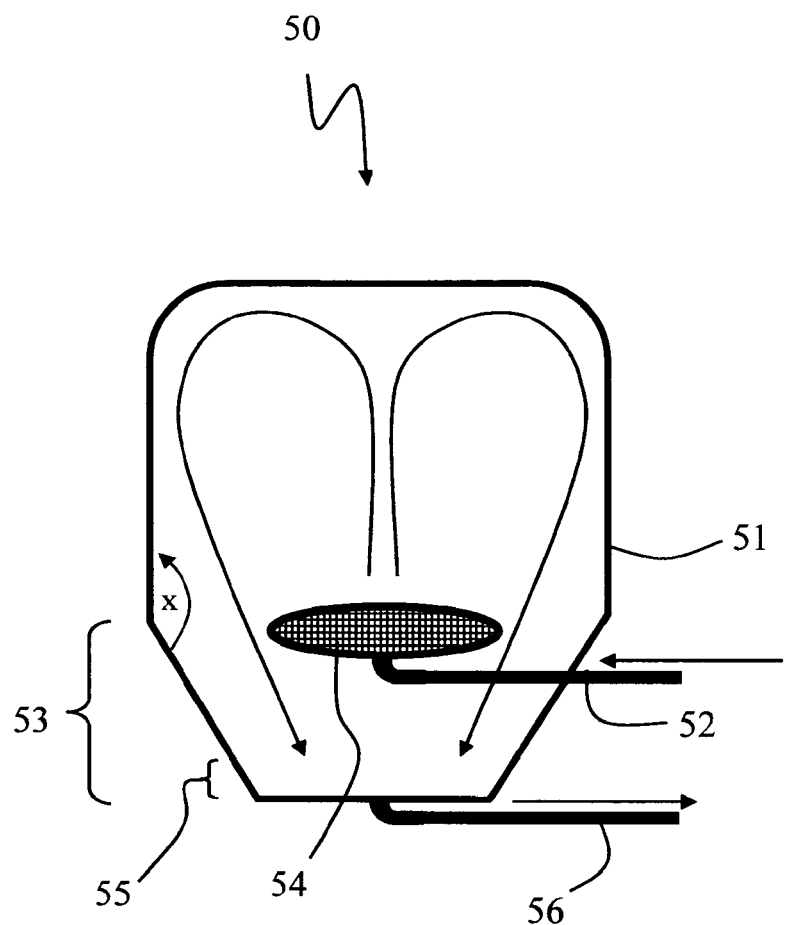
FIG. 4 is a schematic representation of a bioreactor of the present invention.

As a first improvement over conventional systems, a disposable bioreactor, as shown in FIG. 4 generally at 50, is provided having a container 51 with a liquid diffuser 54 disposed therein. A return tube 52 is provided to connect the liquid diffuser 54 with the exterior of the container 51. An outlet tube 56 is also provided to allow for removal of the cell culture from the container 51. The outlet tube 56 and return tube 52 pass through the walls of the container at ports, which can be separate components, or simply be apertures through which the tubes 52, 56 pass. The bioreactor optionally has a tapered portion 53 that results in a narrow lower portion 55 at the bottom of the container 51. The outlet tube 56 can optionally be ported in this narrow lower portion 55.

Bioreactors and bioreactor systems of the present invention are particularly well suited for use with a suspension culture of cells. A suspension culture is one in which all or virtually all of the cells in culture are suspended in a liquid medium rather than adhered to a surface.

Bioreactors and bioreactor systems of the present invention are particularly well suited for use with eukaryotic cells, and, in a preferred embodiment, mammalian cells are used. Examples of useful mammalian cell products include antibodies and viruses. In a preferred embodiment, the bioreactors and bioreactor systems of the present invention are particularly well suited for production of virus in perfusion.

The bioreactor shown in FIG. 4 can be used with any conventional loop-type filtration system, such as the one shown in FIG. 1, by simply attaching the outlet port and return port of the container 51 to the inlet and outlet lines of a pump and filter system. For example, the outlet tube 56 shown in FIG. 4 can be attached to the outlet port of the container 51 and a pump that feeds into a filter as shown in FIG. 1, and the return tube 52 can be connected to the return port of the container that is attached to the liquid diffuser 54 and to the filter opposite the pump. Upon operation of the pump, cell culture will be drawn through the outlet port, into the outlet tube 56, through the pump, through the filter, through the return tube 52, through the return port, and be forced under liquid pressure into the liquid diffuser 54. The liquid diffuser 54 causes the liquid to be diffused and forced upwards in the container. As shown by the arrows, because of the liquid diffuser 54 and container 51, the cell culture develops a flow that reverses and flows downward toward the bottom of the container 51. In embodiments in which a tapered portion 53 is used, the tapering helps to direct the flow of liquid down toward the outlet port and can help accelerate the culture, which can aide in oxygen diffusion and prevent coalescence of gas bubbles. By using the relatively gentle liquid diffuser 54 to provide the mixing needed to maintain oxygen and nutrient distribution throughout the cell culture, the complexity and harshness of an impeller or other complicated systems is obviated. Further, the flow of liquid produced by the liquid diffuser 54 can result in a ripple or wave effect on the exposed surface of the culture within the bioreactor, resulting in improved gas exchange. In further embodiments, the liquid diffuser 54 can be positioned so as to create a fountain effect on the surface of the culture, which aids in aeration.

The container 51 can comprise any suitable disposable material, as is known in the art. The material can be, for example, a polymer, and specifically a thermoplastic polymer that can be formed into a thin, durable, collapsible container. Because a disposable bioreactor can be placed inside of a supporting structure (where a temperature control device can be provided) that approximately matches the external bioreactor shape when full, materials will generally be chosen for their workability and durability. For example, materials that can easily be molded and ported are desirable, for example materials that can be sealed at their edges around ports and/or for which a port welder can be used. Examples of suitable materials include, but are not limited to polyethylene, ethylene vinyl acetate, ethylene vinyl alcohol, polypropylene, nylon, polyester, poly(vinyl chloride) and mixtures of the foregoing. Further examples of suitable materials are given in a 1997 Association of the Advancement of Medical Instrumentation Technical Information Report designated—TIR17-1997, hereinafter referred to as, AAMI 1997.

The container 51 can be formed into any suitable shape, for example, a roughly cylindrical shape, optionally having a tapered portion 53 at the bottom, or conical. As will be recognized by one of skill in the art, many variations are possible and within the scope of this invention. Further, the container 51 can be made to any convenient size, from relatively small bench top type bioreactors to large, industrial scale bioreactors. The valve systems, tubing, pumps, and filters described herein throughout can likewise be increased in size and/or capacity to provide bioreactors and bioreactor systems of various sizes.

The optional tapered portion 53 can be formed as needed to obtain the desired flow. The tapered portion 53 can begin anywhere. In various embodiments, it can begin at any point below the vertical middle of the container 51, and can taper at any angle between 100° and 170° inclusive, as measured as angle x in FIG. 4. The narrow lower portion 55 can have any suitable width, and can be as narrow as the outlet port. In other embodiments, the bioreactor can be formed in a complete cone shape having a continuous taper from the bottom to the top.

The return tube 52 and outlet tube 56 can comprise any suitable material. As will be described below, in various embodiments, the return tube can comprise a rigid material that supports the liquid diffuser 54 centrally in the container 51. The tubes can comprise, for example a thermoplastic polymer, a thermoset polymer, a silicone, or any other suitable material, for example those given in AAMI 1997, among others. If, as in some embodiments, a return port and/or outlet port are separately provided, those ports can also comprise many materials, including many of those just given. In various embodiments, the return tube 52 can comprise a different material on the inside of the container 51 and on the outside of the container. For example, the inside section of the return tube 52 can be a rigid material that is connected to a return port, and the outside section of the return tube 52 can be a flexible material.

The liquid diffuser 54 can comprise any suitable material, including thermoset and thermoplastic polymers and other appropriate materials, such as those given in AAMI 1997. In various embodiments the liquid diffuser will comprise a fairly rigid thermoplastic material that will not distort when subjected to the liquid pressures normally associated with bioreactor systems. When the bioreactor container 51 is full and operational, the liquid diffuser 54 will be held in position within the container 51. The liquid diffuser 54 can be located in various places within the container 51, including located horizontally central or horizontally offset to one side of the container 51. The liquid diffuser 54 can also be positioned vertically within the container 51 to suit a particular need. In various embodiments, for example, the liquid diffuser 54 can be located at the vertical middle of the container 51 or lower. In other embodiments, the liquid diffuser 54 can be located in close proximity to the top of the container 51.

The liquid diffuser 54 can be held in a stable position within the container 51 by many methods. For example, the return tube 52 can be a rigid tube that is securely fastened to the liquid diffuser 52. With the bioreactor in position and filled with a cell culture medium, the externally protruding portion of the return tube 52 can be secured, for example to the bioreactor supporting device, thereby fixing and stabilizing the liquid diffuser 54. In some of these embodiments, the return tube 52 can be ported through the bottom of the container 51, thereby supporting the liquid diffuser 54 in a leg and pedestal type arrangement.

In other embodiments, the liquid diffuser can have one, two, three, four or more supporting fixtures extending radially to the walls of the container, to which the fixtures can be molded or otherwise fixed. In still other embodiments, one, two, three, or four fixtures can be attached to and protrude downward from the liquid diffuser 54 and be attached to the container 51 at its bottom surface. For example, the liquid diffuser 54 can have barb-type fittings that project downward and onto which short pieces of hose are attached, wherein the hoses are attached at their other end to the bottom of the container 51.

In yet another embodiment, the liquid diffuser 54 can be held in position by forming all or a portion of the liquid diffuser 54 from a buoyant material that will tend to rise when submerged in a liquid. One or more tethers comprising a suitable material can then be used to attach the liquid diffuser 54 to the bottom and/or sides of the container. When the bioreactor is filled with liquid in these embodiments, the liquid diffuser 54 will automatically be positioned in the desired location.

The liquid diffusers of the present invention can be formed in many shapes. For example, the liquid diffuser 54 can be formed in the shape of a hollow discus or cylinder that has a port on the bottom or side to accept the return tube and that defines a plurality of openings along the upper surface. For example, the upper surface can define holes, a screen type mesh, or parallel slits, among many other configurations. As used herein, a "liquid diffuser" can be any device that defines more than one aperture through which a liquid culture can be directed toward the top of the container 51, that can be fixed at the end of the return tube 52, and that disburses the return flow of cell culture into a wider, more distributed stream than would occur without the liquid diffuser or with only a simple truncated tube. Examples of such devices include any hollow body rounded shapes having two or more apertures defined in a top surface and hollow body shapes having a screen mesh in the top surface. In various embodiments, the diffuser can be any suitable material, and in particularly preferred embodiments, the diffuser is a hard, molded plastic defining apertures in a top surface.

Figure 6A:
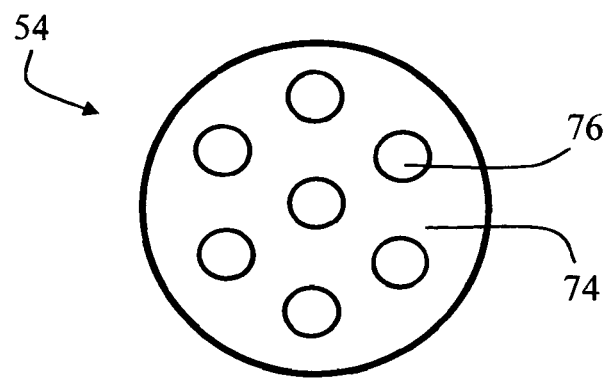
FIGS. 6a and 6b are schematic representations of an example of a liquid diffuser of the present invention.
Figure 6B:
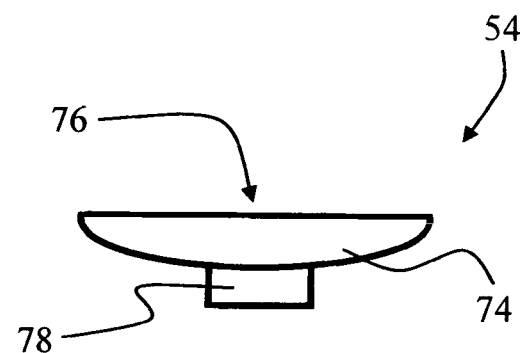

One example of a diffuser is shown schematically in FIGS. 6a and 6b. FIG. 6a shows a schematic top plan view of a liquid diffuser 54 having a hollow body 74 defining multiple apertures 76 in the top surface. FIG. 6b shows the same liquid diffuser 54 wherein an attachment flange 78 is additionally shown. In addition to a bottom, center location, an attachment flange can be situated in any suitable position on the liquid diffuser 54, for example, on the side of the liquid diffuser. The shape of the attachment flange and the liquid diffuser will be selected to achieve both goals of creating an upward flow of culture in the center of the bioreactor while also eliminating or minimizing "dead spots," where fluid flow is undesirably low.

In other embodiments of the present invention, the liquid diffuser described above can be modified with one or more tubes projecting upwards from the hollow body of the liquid diffuser. The tubes can open upwards, or can define apertures or slits in the side walls that direct fluid flow at an angle that is less than directly vertical. For example, tubes having o-rings and ¼ turn lock in place fittings could be used, and 2-6 central tubes projecting upwards can be surrounded by 4-10 tubes that direct flow at an angle less than vertical. Additionally, one or more apertures may be defined in the liquid diffuser hollow body itself.

In further embodiments, a gas diffuser and liquid diffuser are integrated into a single unit that can be any of the embodiments described herein for a liquid diffuser. Gas and liquid can be directed to the combined unit through a single, shared line, which would increase mixing, or can be fed to the unit separately and combined within the hollow body of the liquid diffuser.

In yet a further embodiment a ring shaped gas diffuser is placed above the liquid diffuser so as to allow the fluid stream to pass through the gas diffuser during its vertical movement, which results in concurrent mixing.

Figure 5:
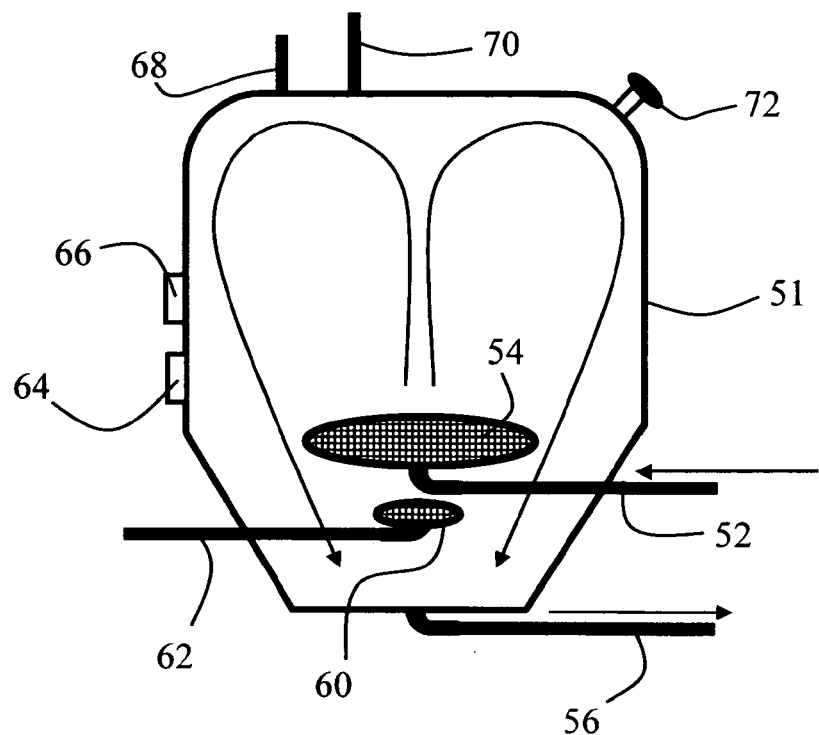
FIG. 5 is a schematic representation of a bioreactor of the present invention.

As shown in FIG. 5, disposable bioreactors of the present invention can additionally comprise various other conventional components.

In various embodiments of the present invention, a gas diffuser 60 and gas diffuser tube 62 are included to provide, among other things, air and other gasses, such as oxygen, and additional mixing. In the configuration shown in FIG. 5, the gas diffuser 60 is located horizontally central in the container 51 and beneath the liquid diffuser 54. In this configuration, the gas emitted by the gas diffuser 60 will bubble up around the liquid diffuser 54, which will both add vigor to the mixing and reinforce the counter current that occurs as a result of the liquid diffuser 54 and flow to the outlet tube 56. In other embodiments, the gas diffuser 60 can be offset relative to the liquid diffuser 54, or located above the liquid diffuser 54.

As shown in FIG. 5, a pH sensor 64 and dissolved oxygen sensor 66 can also be included in the bioreactor. A glucose sensor (not shown) can also be included. Other sensors can be included, as desired. The sensors can be located in any convenient position on the container 51.

Pressure sensors can also be used in systems of the present invention as are known in the art. For example, pressure sensors can be positioned on the filter and the filter feed line to determine filtrate pressure and feed pressure, as well as transfilter pressure, which is the difference between the two pressures. A further pressure sensor can be added, as desired to measure return pressure in the return tube.

A port and/or a media feed container tube 68 and a port and/or a base container tube 70 can also be included to allow for the addition of media or pH controller or other additives as needed. Again, the ports and/or tubes can be located in any convenient location in the container 51. Further ports can be added for adding antifoam and other components, as are known in the art.

A vent with or without a filter 72 can be included in any convenient location. The vent can be used for venting gasses, known as "off-gases," that are produced by the growing culture. These off-gases can be analyzed as a process sensing means, which is non-intrusive and does not require sterilization. A pressure relief valve can also be included.

A further optional component is a flexible container to bleed off the culture, which can also function as a transfer bag (not shown). This flexible container is generally connected to the bioreactor at a low point on the bioreactor, for example near the outlet tube 56.

As with any conventional bioreactor, control systems for receiving inputs from the sensors and for automatically adding media or base as required, for example, can also be added to bioreactors of the present invention, as desired.

The above-described embodiments of a bioreactor of the present invention, as noted, can be used with any conventional loop type bioreactor filtration system by simply attaching the outlet and return tubes or ports to the appropriate pump and filter system.

Bioreactors of the present invention do not require a moving impeller or motion platforms. Consequently, the bioreactors of the present invention provide a simple, efficient device for growing cell cultures. Further, because the bioreactors of the present invention can be fabricated from relatively inexpensive materials that can be pre-sterilized with, for example, gamma radiation or ethylene oxide (ETO), they are relatively inexpensive and can be used as a disposable bioreactor that eliminates the need for costly and time consuming sterilization and cleaning. Bioreactors can also be provided in a ready-to-sterilize condition, with the end user performing the sterilization step.

Any of the bioreactors or bioreactor systems disclosed herein can be used in conjunction with an electronic controller, as are known in the art. Controllers can be configured to suit particular culture needs, and, for example, can be configured to monitor all sensors, pressures throughout the system, and pump speeds and cycles, among others.

In various embodiments, an optional, integral, sterilized back-up filter module is included. This back-up filter module is in place from the beginning of a run, but the feed to/from the filter is pinched off. When the filter modules needed to be switched, the tubing pincher is removed and placed on a tube leading to/from the old filter and flow through the new filter would commence.

The present invention further includes various methods for using the bioreactors described herein.

The present invention includes a method of growing eukaryotic cells using any of the bioreactors of the present invention, comprising the steps of inoculating media in a bioreactor with a eukaryotic cell culture, and growing the culture in the bioreactor in perfusion or in a batch culture. The method of growing eukaryotic cells can further comprise the step of separating a desired component of the culture from the culture using one of the separation techniques described herein, for example, using a hollow fiber filter.

The present invention includes a method of growing eukaryotic cells and separating out from the culture viral vectors (virus) or secreted biomolecules.

The present invention includes a method of growing eukaryotic cells for collection and use of those eukaryotic cells.

The present invention includes a method of growing a mammalian cell, comprising any of the methods described herein for cellular growth or component separation.

The present invention includes a method of growing an insect cell for producing proteins, comprising any of the methods described herein for cellular growth or component separation.

The present invention includes a method of producing an antibody, comprising any of the methods described herein for cellular growth or component separation.

In addition to their use with conventional loop-type systems, bioreactors of the present invention can be used with diaphragm-type filtration systems such as the one shown in FIG. 3 by incorporating a valving system of the present invention, as described herein.

Figure 7:
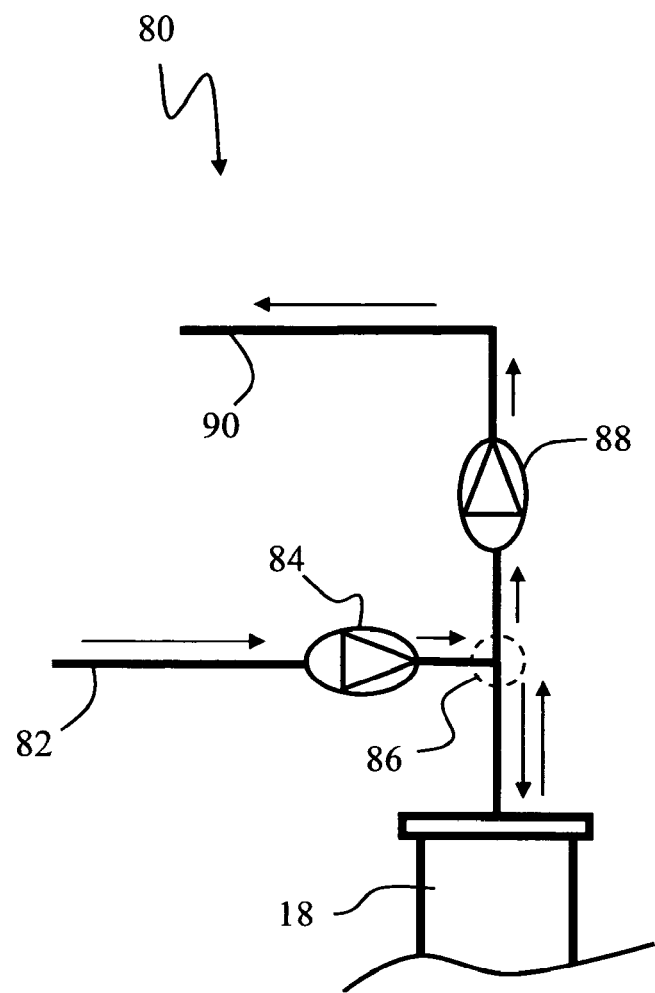
FIG. 7 is a schematic representation of a bioreactor valve system of the present invention.

As shown in FIG. 7 generally at 80, which shows a schematic illustration of a valving system of the present invention, a diaphragm pump system can be modified for use with the bioreactors of the present invention. Additionally, the valving system shown in FIG. 7 and described below can be used independently of the bioreactors of the present invention. That is, any conventional bioreactor having an outlet and a return, for example the loop system shown in FIG. 1, will be compatible with the valving system shown in FIG. 7 and a diaphragm pump and filter system. In further embodiments of the present invention, a diaphragm pump can be used in the manner shown in FIG. 7 without the use of a filter. In this configuration, the diaphragm pump and valve system provide culture mixing without simultaneously using a filter adjacent the diaphragm pump, which is particularly useful, for example, for a batch culture in which no filtration during cell growth is desired.

As shown in FIG. 7, an outlet tube 82 is connected to a first unidirectional valve 84. This first valve is unidirectional, which, as used herein, means that the valve only allows liquid to flow through in a single direction. When the diaphragm pump (not shown) is in the reduced pressure mode, liquid will be drawn from the bioreactor, through the outlet tube, through the first unidirectional valve 84, though a connector 86, and into the filter 18 toward the diaphragm pump. Because the second unidirectional valve 88 will not permit flow back toward the filter 18 from the return tube 90, virtually all of the fluid that is drawn into the filter is derived from the outlet tube 82. Upon reversal of the pressure in the diaphragm pump, the fluid being expelled from the filter 18 cannot move past the first unidirectional valve 84, and is instead forced through the second unidirectional valve 88, into the return tube 90, and back to the bioreactor.

In any embodiments of the present invention in which a filter, and specifically a hollow fiber filter, is used, there are equivalent embodiments in which a continuous flow centrifuge or a settling device is used, where applicable.

The tubes and connector used in these embodiments can comprise any suitable material, as described elsewhere herein, and specifically as disclosed in AAMI 1997. In various preferred embodiments, the tubes comprises weldable tubing or silicon tubing. Weldable tubing, which can be sterilely connected using a heat welding device, includes thermoplastic elastomeric tubing, as is known in the art, such as C-Flex® and PharMed® tubings.

The valves can be any valve that is compatible with the other components of the system and that can function to allow flow in only one direction. Examples of suitable unidirectional valves include any conventional check valves, which are commercially available as individual components or prefabricated inline in a tube. Also specifically included are valves that are controlled so as to afford unidirectional flow, for example, a solenoid driven valve or pinch valve that is controlled in concert with the diaphragm pump so as to afford flow in one direction.

Although FIG. 7 shows one possible arrangement of valves and tubing that accomplish the inventive method of modifying a diaphragm pump type filter system for use in a separate return and outlet type bioreactor, one skilled in the art will recognize that there are many means for both connecting the valves to a bioreactor as well as many means for connecting the valves to one end of a filter installed on a diaphragm pump.

Figure 8:
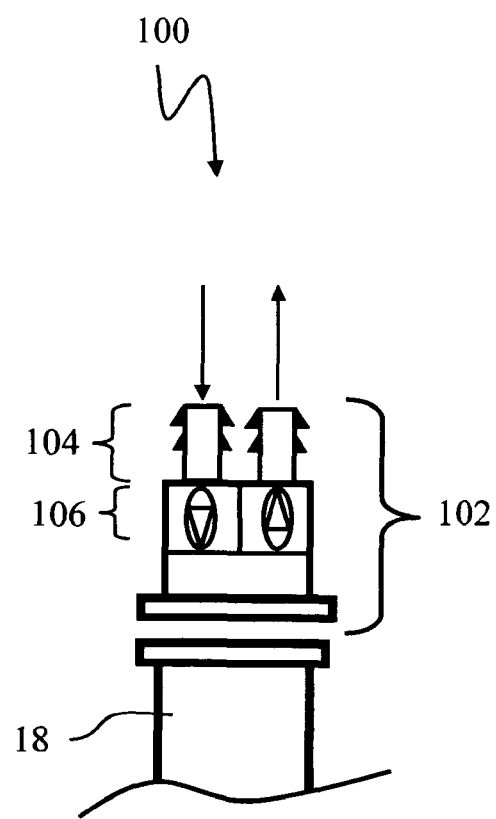
FIG. 8 is a schematic representation of a bioreactor valve system of the present invention.

One example is shown in FIG. 8 generally at 100, where the means for connecting the valves to a filter attached to a diaphragm pump is a single integrated valve unit 102 that has a single housing in which first and second unidirectional valves 106 are housed. Barb fittings 104 are shown as an example of how such an integrated valve unit 102 could be connected to outlet and return tubes. As can be further seen, the integrated valve unit eliminates the need for a connector 86 (as shown in FIG. 7), and eliminates the possible need for connector 86. In another, similar embodiment, the integrated valve unit 102 can be added as a permanent fitting on, or molded as a part of, the filter 18. These embodiments offer the additional advantage of removing the joint between the integrated valve unit 102 and the filter 18. As another alternative embodiment, the first and second valve can be combined in a flip flop type or three-way valve that is either mechanically controlled by fluid pressure, or otherwise controlled to correspond to the change in liquid flow though the filter. Such a valve can, for example, be controlled by a solenoid that directs fluid flow though one of two ports.

A further example of means for connecting the valves to the bioreactor include disposing the valves or an integrated valve unit directly in a port or connector on the bioreactor container. For example, check valve fittings can be fixed and sealed into the wall of a bioreactor. Tubes, can then be used to join each valve to a connector, such as the one shown in FIG. 7 as 86, which leads to one end of a filter that is attached at the other end to a diaphragm pump.

In another embodiment, an integrated valve unit, such as the one shown in FIG. 8 as 102, either connected to or integrated with a filter connected to a diaphragm pump, can be directly connected to the bottom of a bioreactor. For example, a bioreactor of the present invention in which the liquid diffuser is disposed on a rigid tube extending to the bottom of the bioreactor container could be used. In these embodiments, the filter and diaphragm pump would hang downward from the bioreactor and be directly connected to it, with little or no tubing required.

As will be recognized by those of skill in the art, the valving systems shown in FIG. 7 and FIG. 8, as well as the above-described systems, provide significant advantages. For example, a conventional bioreactor that has been designed for use in a loop system can, with an appropriately chosen valving system of the present invention, be used with a diaphragm pump and filter system. Further, the valving systems shown and described results in a much greater turnover of fluid in the filter because a significantly greater amount of fluid drawn into the filter is freshly derived from the bioreactor container with each cycle of the diaphragm pump.

A further use of the described valving systems is as an upgrade on an existing reverse cross flow system using a diaphragm pump and a single outlet and return tube. In these systems, a second port can be added to the bioreactor to allow for a second tube to be added to the system. As another alternative, a single port can be made to function more efficiently by adding a split connector to the single port and placing two unidirectional valves on either opening of the split connecter, where each of the valves is connected to a hose that leads to one of the unidirectional valves close to the filter or valves that are integrated into a unit at the filter. In this manner, the distance between the single port and the filter is essentially divided into an outlet tube and a return tube, thereby making the system more efficient at recirculating fluid. In other embodiments, this arrangement can be modified to have only a single unidirectional valve in each of the outlet and return tubes. In further embodiments, a three way valve is installed on a bioreactor port, and two tubes are used to connect the three way valve to a tee connector disposed on a filter or connected to a filter with a tube.

The present invention includes a method of directing fluid flow to and from a bioreactor, or within a bioreactor system, comprising using any of the valving systems of the present invention, as described herein.

The present invention includes a method for improving flow in a bioreactor system using a diaphragm pump and tangential flow filtration, comprising disposing a valving system of the present invention between said diaphragm pump and a bioreactor, and, using said diaphragm pump to pump culture to and from said bioreactor through said valving system.

Figure 9:
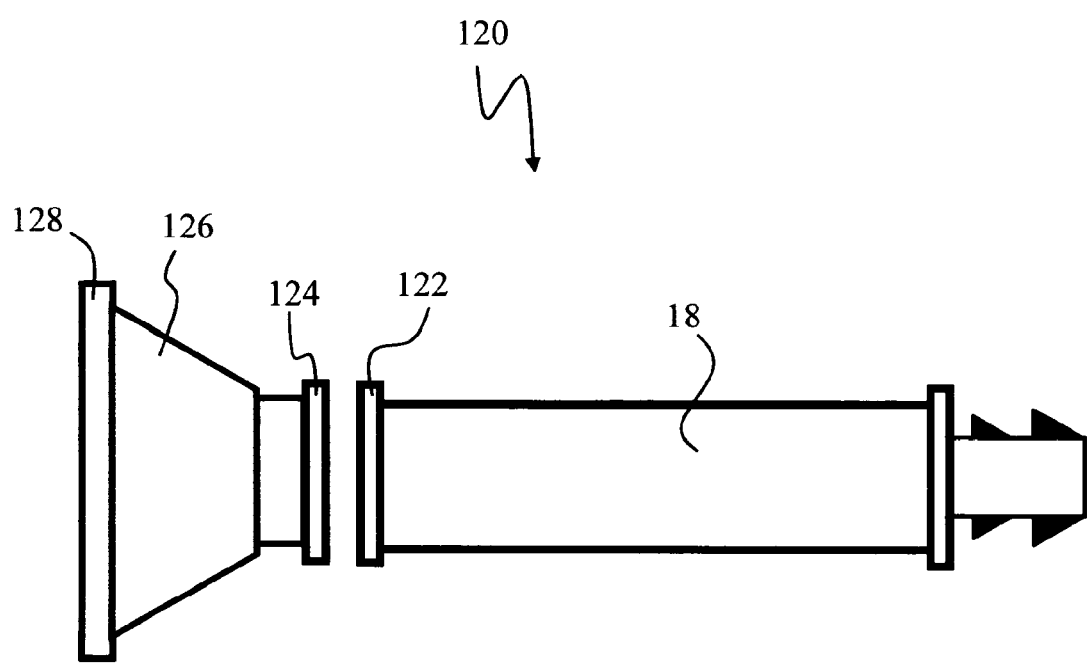
FIG. 9 is a schematic representation of a conventional diaphragm pump/filter housing arrangement.

The present invention also includes a disposable filter. As shown generally at 120 in FIG. 9 in a non-spherical shape, a conventional diaphragm pump and filter arrangement, such as those disclosed in U.S. Pat. No. 6,544,424, can require the joining of a filter 18 to the liquid-containing side 126 of the diaphragm pump. This joining is typically accomplished by fastening a TriClamp® or similar clamp over a filter flange 122 and a first pump flange 124. A second pump flange 128 allows the liquid-containing side 126 of the diaphragm pump to be connected to the gas-containing side of the diaphragm pump (not shown), for example, with bolts and nuts or clamps. In this conventional arrangement, the diaphragm pump consists of stainless steel and is intended for long term use. This necessitates cleaning and sterilization after each use, which reduces the efficiency of the system.

Figure 10:
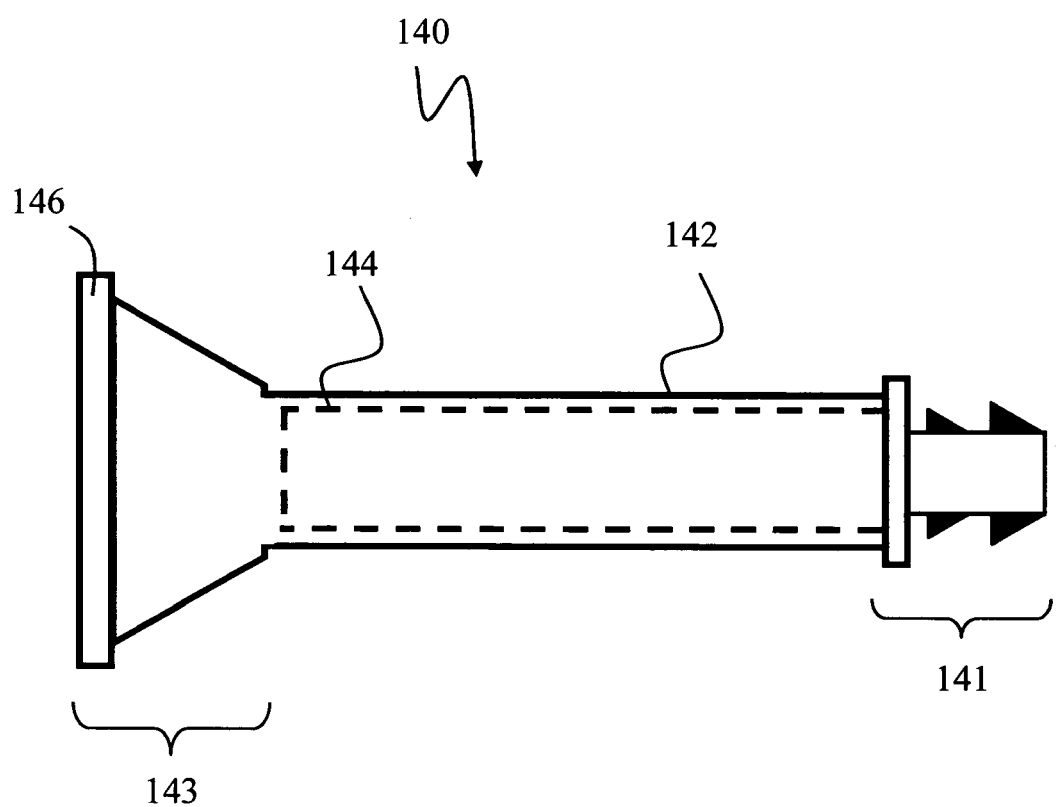
FIG. 10 is a schematic representation of a filter of the present invention.

As shown in FIG. 10 generally as 140, in various embodiments disposable filters of the present invention comprise a filter housing 142 having an open first end 141, an open second end 143, and a filter element 144 disposed within the filter housing. A port and/or tube for removing filtrate and optional ports, for example sampling ports, are not shown in the Figure. The open first end 141 is a conventional filter end, and can be, for example, any standard connector, such as a barb fitting, which would allow a direct connection to tubing, or, in some embodiments, a luer fitting.

The open first end can be formed as continuous with the rest of the filter housing 142, or as a fitting that is fixed and sealed onto the filter housing 142. The open first end 141 is said to be open because fluid can pass into the filter element 144 through this end.

In these embodiments, the open second end 143 is formed in the shape of a liquid-containing side of a diaphragm pump, and, similar to the open first end 141, can be molded continuous with the filter housing or can be attached and sealed as a fitting. The open second end 143 is said to be open because fluid can pass into the filter element 144 through this end. The open second end 143 can have a flange 146 or other means for connection with the gas-containing side of a diaphragm pump. The flange 146 can have holes drilled therethrough, for example, to allow for bolt and nut attachment. In other embodiments, clamps can be used to secure the two parts.

The filter housing 142 can comprise any suitable material that is compatible with the other components of the filter. Examples of useful materials include thermoplastic polymers, and specifically rigid thermoplastic polymers, for example, those given in AAMI 1997.

The filter element 144 can be any filter element that is suitable for use in a diaphragm pump bioreactor system. In various embodiments, the filter element 144 is a hollow fiber filter element. Useful filtration pore sizes are, for example, from 100,000 nominal molecular weight cut-off to 1 micron, with molecular weight cut-offs as low as 1,000.

The open second end 143, although shown in an exemplary "top hat" shape, can be formed in any shape that roughly emulates that of the liquid-containing side of any given suitable diaphragm pump. Further, the open second end 143 can be any suitable size that allows for proper recirculation of the fluid out of the pump and connecting tubes.

In various embodiments, the open second end will be formed into a shape that allows for full extension of the membrane into the open second end without causing the membrane to fully contact the inside walls of the open second end. This clearance prevents or reduces mechanical damage to cells and cellular components that can otherwise occur. For example, for embodiments in which the open second end and the gas-containing side of the diaphragm pump are both roughly hemispherical, the radius of the hemisphere defined by the open second end can be greater than the radius of the hemisphere defined by the gas-containing side of the diaphragm pump.

Although a gas line driven diaphragm pump is shown herein throughout as an exemplary diaphragm pump, piston driven and mechanically driven diaphragm pumps can also be used in any of the embodiments of the present invention in which a diaphragm pump is used. Further, for embodiments of the present invention in which a diaphragm pump is used, any suitable, conventional membrane can be used, including membranes comprising silicone.

The integration of the liquid-containing side of a diaphragm pump into a filter offers significant advantages. Because the open second side replaces the liquid-containing side of the diaphragm pump, a joint between the pump and the filter is eliminated. Further, the added portion of the open second side of the filter can be manufactured from relatively inexpensive materials such as rigid plastics, which increases the cost of manufacturing the filter only marginally over conventional filters. As opposed to conventional systems, where only the filter is discarded and the liquid-containing side of the diaphragm pump must be washed and sterilized, the disposable filters of the present invention can be discarded after use, eliminating any need to clean and sterilize the diaphragm pump.

In some embodiments of the present invention, an all plastic diaphragm pump can be used. In these embodiments, both halves—32 in FIG. 3 in combination with 140 in FIG. 10—of the pump can be plastic. In these embodiments, the two parts can be provided in a manner whereby the two parts are held together so as to be ready for sterilization by irradiation or ETO. In one example, tape can be used to temporarily seal and hold the two parts, which can be arranged with a membrane in place, and an end user can join the two parts with, for example, clamps or bolts and nuts. In another embodiment, ultrasound welding can be used to simultaneously join and seal the two parts, which can then be provided in a ready-to-irradiate condition. Irradiation can be performed, for example, using industry standard guidelines.

The present invention includes a method of filtering a culture, comprising using any of the disposable filters of the present invention.

The present invention includes a method of filtering a culture, comprising disposing a disposable filter of the present invention in position on a diaphragm pump, connecting the disposable filter to a liquid culture, and operating said diaphragm pump.

The present invention also includes filtration systems having at least two of the following: A) any bioreactor of the present invention having a liquid diffuser B) any bioreactor valving system of the present invention, and C) any disposable filter of the present invention. In these systems and any of the components described herein that are within the scope of the present invention, scalability is readily achieved by increasing the size and/or capacity of the various components. For example, for a larger bioreactor, larger tubing, valves, pumps, and hollow fiber filters can be used to accommodate the increased volume of cell culture. As a further example, multiple filters and/or pumps can be placed in series or in parallel to increase the filtering capacity without increasing the size of the filters.

The present invention includes a method of growing a eukaryotic cell culture, comprising using the filtration system described in the preceding paragraph.

By virtue of the present invention, bioreactors, bioreactor systems, bioreactor valving systems, and hollow fiber filters are provided that allow for the efficient and economical growth and filtration of a cell culture. The bioreactors and systems disclosed herein allow, for example, efficient perfusion growth of an antibody and virus production with total containment and low shear. Further, excellent viral production can be achieved with systems of the present invention, and specifically with properly sized hollow fiber filters.

Although embodiments of the present invention have been described in various embodiments, it will be clear to those of ordinary skill in the art that many other permutations are possible and are within the scope and spirit of the present invention.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed as the best mode contemplated for carrying out this invention, but that the invention will include all embodiments falling within the scope of the appended claims.

It will further be understood that any of the ranges, values, or characteristics given for any single component of the present invention can be used interchangeable with any ranges, values, or characteristics given for any of the other components of the invention, where compatible, to form an embodiment having defined values for each of the components, as given herein throughout. For example, a diaphragm pump of any of the particular sizes given can be combined, where appropriate, with a bioreactor of any of the sizes given to form a bioreactor system having the detailed parameters of both the pump and the bioreactor, thereby forming many permutations that are within the scope of the present invention.

Any figure reference numbers given within the abstract or any claims are for illustrative purposes only and should not be construed to limit the claimed invention to any one particular embodiment shown in any figure.

Unless otherwise noted, drawings are not drawn to scale.

Each reference, including journal articles, patents, applications, and books, referred to herein is hereby incorporated by reference in its entirety.

What is claimed is:

1. A bioreactor, comprising:
 a container for holding a fluid culture;
 a first unidirectional valve connected to an outlet of the container;
 a second unidirectional valve connected to an inlet of the container;
 a connector having a first lead connected to the first unidirectional valve, a second lead connected to the second unidirectional valve and a third lead;
 a filter having a first end connected to the third lead of the connector; and
 a diaphragm pump connected to a second end of the filter and in fluid communication with the first and second valves, wherein the first unidirectional valve allows fluid culture flow away from the container and toward the diaphragm pump and the second unidirectional valve allows fluid culture flow toward the container and away from the diaphragm pump.

2. The bioreactor of claim 1, wherein the container comprises a disposable container for holding a fluid culture, the container including a diffuser completely disposed within the fluid culture when held within the disposable container, an outlet tube for drawing the culture from a bottom of the container, and an inlet tube for returning at least a portion the culture from the outlet tube to the container through the diffuser, wherein the diffuser disperses the returning culture to the disposable container into a wider more distributed stream than would occur using the inlet tube without the diffuser.

3. The bioreactor of claim 2, wherein the diffuser combines a gas from a source external to the container with the returning culture before the dispersion to the container.

4. The bioreactor of claim 2, wherein the first diffuser and at least one of the tubes comprise a thermoplastic or silicon.

5. The bioreactor of claim 2, wherein the container tapers to a narrow lower portion and the outlet tube is disposed in the narrow lower portion.

6. The bioreactor of claim 2, wherein the first diffuser comprises a screen mesh.

7. The bioreactor of claim 2, wherein the first diffuser comprises a hollow body having a top surface, wherein the hollow body defines a plurality of apertures extending through the top surface.

8. The bioreactor of claim 2, further comprising a second diffuser disposed below the first diffuser.

9. The bioreactor of claim 8, wherein the second diffuser is a gas diffuser, whereby bubbles from the second diffuser will bubble up around the first diffuser.

10. The bioreactor of claim 1, wherein the first unidirectional valve and the second unidirectional valve are coupled to at least one of the diaphragm pump and the container by tubing.

11. The bioreactor of claim 10, wherein the tubing comprises a weldable thermoplastic elastomer or silicone.

12. The bioreactor of claim 1, wherein at least one of the first unidirectional valve and the second unidirectional valve are at least one of a pinch valve and a check valve.

13. The bioreactor of claim 1, further comprising:
 a filter housing having an open first end and an open second end, the open second end being formed as the liquid-containing side of a diaphragm pump; and,
 a filter element disposed in the filter housing.

14. The bioreactor of claim 13, wherein the filter element comprises hollow fibers.

15. The bioreactor of claim 13 wherein the open second end is formed in an approximately semi-hemispherical shape.

16. The bioreactor of claim 1, further comprising at least one pH sensor, dissolved oxygen sensor and a glucose sensor.

17. A filtration system, comprising:
 A) a bioreactor, comprising:
  a container for holding a fluid culture;
  a filter for filtering the fluid culture; and
 B) a bioreactor valve system disposed between the container and the filter, the bioreactor valve system comprising:
  a first unidirectional valve coupled to an outlet of the container;
  a second unidirectional valve coupled to an inlet of the container;
  a connector having a first lead connected to the first unidirectional valve, a second lead connected to the second unidirectional valve and a third lead connected to a first end of the filter; and
  a diaphragm pump connected to a second end of the filter, wherein the first unidirectional valve allows liquid flow away from the bioreactor and toward the diaphragm pump and the second unidirectional valve allows liquid flow toward the bioreactor and away from the diaphragm pump.

18. The filtration system of claim 17, wherein the bioreactor further includes a diffuser disposed completely within the fluid culture held in the container;
 an outlet tube for drawing the culture from a bottom of the container;
 an inlet tube for returning at least a portion the culture from the outlet tube to the container through the diffuser, the diffuser being disposed above the container bottom and adapted to lie within the culture, wherein the diffuser disperses the returning culture to the disposable container into a wider more distributed stream than would occur using the inlet tube without the diffuser, wherein the diffuser combines a gas from a source external to the container with the returning culture before the dispersion to the container.

19. The filtration system of claim 18, wherein at least a portion of the first diffuser is formed from a buoyant material.

20. A bioreactor, comprising:
 a container for holding a fluid culture;
 a single integrated valve unit including a first unidirectional valve connected to an outlet of the container and a second unidirectional valve connected to an inlet of the container;
 a filter having a first end coupled to the single integrated valve unit; and
 a diaphragm pump connected to a second end of the filter and in fluid communication with the single integrated valve unit, wherein the first unidirectional valve allows fluid culture flow away from the container and toward the diaphragm pump and the second unidirectional valve allows fluid culture flow toward the container and away from the diaphragm pump.

21. The bioreactor of claim 20, wherein the single integrated valve unit comprises a single housing having a first barb fitting connected via tubing to the outlet of the container and a second barb fitting connected via tubing to the inlet of the container, the housing being coupled to the first end of the filter.

* * * * *